US006255414B1

(12) United States Patent
Ittel et al.

(10) Patent No.: US 6,255,414 B1
(45) Date of Patent: Jul. 3, 2001

(54) POLYMERIZATION OF OLEFINS

(75) Inventors: Steven Dale Ittel, Wilmington, DE (US); Edward Bryan Coughlin, Amherst, MA (US); Ying Wang, West Chester, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/383,900

(22) Filed: Aug. 26, 1999

Related U.S. Application Data
(60) Provisional application No. 60/098,668, filed on Sep. 1, 1998.

(51) Int. Cl.$^7$ ................................. C08F 4/16; C08F 4/60
(52) U.S. Cl. .................. 526/115; 526/172; 526/281; 526/335; 526/346; 526/352; 526/161; 526/116; 526/117; 526/119; 502/117; 502/162
(58) Field of Search ........................ 526/161, 348.6, 526/128, 172, 352, 346, 335, 281; 502/164, 117, 162

(56) References Cited

FOREIGN PATENT DOCUMENTS

| 0 763 550 A1 | * | 3/1997 | (EP) | ................ | C08F/10/00 |
| 10036424 | | 2/1998 | (JP) | ................ | C08F/10/00 |
| WO 99/50318 | | 10/1999 | (WO) | ................ | C08F/10/00 |

OTHER PUBLICATIONS

Adam Littke et al., Bulky Bis(alkylamidinate) Complexes of Group 4. Synthesis and Characterization of M(CyNC(R')NCy)$_2$Cl$_2$ and Zr(CyNC(Me)NCy)$_2$Me$_2$ (R'=Me, M=Ti, Zr, Hf; R'=$^t$Bu, M=Zr), *Organometallics*, 17, 446–451, 1998 (No Month).

Victoria Volkis, et al., Pressure Modulates Stereoregularities in the Polymerization of Propylene Promoted by rac–Octahedral Heteroallylic Complexes, *Organometallics*, 17, 3155–3157, 1998 (No Month).

Sarah L. Aeilts, et al., Aluminum Alkyl Complexes Containing Guanidinate Ligands, *Organometallics*, 17, 3265–3270, 1998 (No Month).

Peter J. Stewart et al., New Titanium Complexes Containing an Amidinate–Imide Supporting Ligand Set: Cyclopentadienyl, Alkyl, Borohydride, Aryloxide, and Amide Derivatives, *Organometallics*, 17, 3271–3281, 1998 (No Month).

Herskovics–Korine et al., Bis(trimethylsilyl) benzamidinate zirconium dichlorides. Active catalysts for ethylene polymerization, *Journal of Organo metallic Chemistry*, 503, 307–314, 1995 (No Month).

Juan C. Flores et al., (N,N'–Dimethyl–p–toluamidinato)trichlorotitanium: Synthesis, Structure, and Polymerization Catalysis, *Organometallics*, 14, 2106–2108, 1995 (No Month).

H. W. Roesky, et al., Benzamidinato complexes of main group and transition metals–Crystal structures of PhC(NsiMe$_3$)$_2$TiCl$_2$ and PhC(NsiMe$_3$)$_2$MoO$_2$., *Chem. Ber.*, 121, 1403–1406, 1988 (No Month).

M. Busch et al., Magnesium halogen alkyl and carbodiimides, *Communication from the chemical laboratory of the University of Erlangen, Germany*, 40, 4296–4298, 1907 (No Month).

* cited by examiner

Primary Examiner—David W. Wu
Assistant Examiner—R. Harlan

(57) ABSTRACT

Olefins such as ethylene and propylene may be polymerized by using as catalysts novel selected transition metal complexes of bis(carboximidamidatonates) in which the carboximidamidatonate groups are connected together through covalent bonds by a bridging group. The resulting polymers are useful as molding and extrusion resins.

42 Claims, No Drawings

POLYMERIZATION OF OLEFINS

This application claims priority under 35 U.S.C. §119 from U.S. Provisional Application Ser. No. 60/098,668 (filed Sep. 1, 1998), which is incorporated by reference herein as if fully set forth.

FIELD OF THE INVENTION

Olefins are polymerized by using as polymerization catalysts certain novel transition metal complexes of selected bis(carboximidamidatonates).

TECHNICAL BACKGROUND

The polymerization of olefins such as ethylene, propylene, norbornene and cyclopentene are very important commercial processes. These are most commonly done using polymerization catalyst systems containing certain transition complexes. For instance, the Zielger-Natta-type catalysts and metallocene-type catalysts are some of the more important and well-known catalysts of this type which are used to make billions of kilograms of polyolefins annually. Due to the importance of the polymerization of olefins, new catalyst systems are constantly being sought.

Japanese Patent Application 10/36,424 shows a formula for a bis(carboximidamidatonate), but neither describes how to make such a compound nor actually does a polymerization with such a compound.

A. Littke, et al., Organometallics, vol. 17, p. 446–451 (1998); V. Volkis, et al., *ibid*, p. 3155–3157; J. C. Flores, et al., Organometallics, vol. 14, p. 2106–2108 (1995); P. J. Stewart, et al., *ibid*, p. 3271–3281; H. W. Roesky, et al., Chem. Ber., vol. 121, p. 1403–1406 (1988); and D. Herskovics-Korine, et al., J. Organometal. Chem., vol. 503, p. 307–314 (1995); report the synthesis and/or use of transition metal complexes of two independent (mono) carboximidamidatonate ligands as polymerization catalysts. However, in none of these references are the two carboximidamidatonates groups joined by a common moiety such as a benzene ring.

A. Littke, et al., Organometallics, vol. 17, p. 446–451 (1998) and S. L. Aelits, et al., *ibid*, p. 3265–3270, describes the formation of carboximidamidatonates by the reaction of an organometallic compound with a carbodiimide. The use of a bis(alkyl metal salt) to form a bis(carboximidamidatonate) is not described.

SUMMARY OF THE INVENTION

This invention concerns a first process for the polymerization of olefins, comprising the step of contacting, at a temperature of about −50° C. to about +250°C.:

(a) an olefin selected from the group consisting of an α-olefin, a styrene, a cyclopentene, and a norbornene; and (b) a first compound of the formula (X)

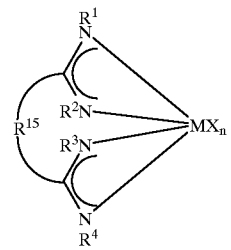

(X)

wherein:
$R^1$, $R^2$, $R^3$ and $R^4$ are each independently hydrocarbyl, substituted hydrocarbyl or silyl;
$R^{15}$ is a divalent organic moiety;
each X is independently an anion;
n is an integer equal to the valence of M minus 2; and
M is Ti, Zr, Hf, V, Cr, Sc, Y or a rare earth metal.

Optionally, the olefin, first compound and a second compound W may be contacted, which second compound W is a neutral Lewis acid capable of abstracting an $X^-$ from the first compound to form $WX^-$, provided that the anion formed is a weakly coordinating anion, or a cationic Lewis or Bronsted acid whose counterion is a weakly coordinating anion; and provided that when none of X is alkyl, acyl or hydride, said second compound is capable of transferring hydride or alkyl to M.

This invention also concerns the first compound (X) described above.

In another aspect, the present invention concerns a second process for the polymerization of olefins, comprising the step of contacting, at a temperature of about −50° C. to about +250° C., a transition metal complex of a ligand of the formula

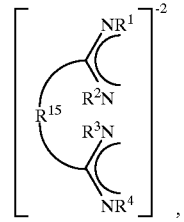

(XI)

with an olefin, wherein:
said olefin is selected from the group consisting of an α-olefin, a styrene, a cyclopentene, and a norbornene;
said transition metal is Ti, Zr, Hf, V, Cr, Sc, Y or a rare earth metal;
$R^1$, $R^2$, $R^3$ and $R^4$ are each independently hydrocarbyl, substituted hydrocarbyl or silyl; and
$R^{15}$ is a divalent organic moiety.

The present invention further concerns an anion which is the ligand of the formula (XI) described above.

In yet another aspect, the present invention concerns a process for preparing a transition metal complex of a bis(carboximidamidatonate), such as used in the first and second processes described above, comprising the step of reacting a salt of said transition metal with a dialkali metal salt and/or alkaline earth metal salt of a bis(carboximidamidatonate).

Still further, the invention concerns a process for the production of a bis(carboximidamidatonate), comprising the step of reacting a bis(alkyl metal salt) with 2 moles of a carbodiimide.

DETAILS OF THE INVENTION

Herein certain terms are used to define certain chemical groups or compounds. These terms are defined below.

By a carboximidamidatonate group is meant a group of the formula (IX)

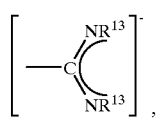

(IX)

wherein each $R^{13}$ is independently hydrocarbyl, substituted hydrocarbyl or silyl. A bis (carboximidamidatonate) has two such groups in the molecule.

By a bis(alkyl metal salt) is meant a compound which has 2 alkyl carbon atoms which each have a single negative charge and are anions of or associated with one or more metal cations in such a way that the positive charge on the metal cation(s) is balanced by the 2 negative charges on the anion.

A "hydrocarbyl group" is a univalent group containing only carbon and hydrogen. If not otherwise stated, it is preferred that hydrocarbyl groups herein contain 1 to about 30 carbon atoms.

By "substituted hydrocarbyl" herein is meant a hydrocarbyl group which contains one or more substituent groups which are inert under the process conditions to which the compound containing these groups is subjected. The substituent groups also do not substantially interfere with the process. If not otherwise stated, it is preferred that substituted hydrocarbyl groups herein contain 1 to about 30 carbon atoms. Included in the meaning of "substituted" are heteroaromatic rings. All of the hydrogen atoms in the substituted hydrocarbyl may be substituted for, such as in trifluoromethyl.

By relatively noncoordinating (or weakly coordinating) anions are meant those anions as are generally referred to in the art in this manner, and the coordinating ability of such anions is known and has been discussed in the literature, see for instance W. Beck., et al., Chem. Rev., vol. 88 p. 1405–1421 (1988), and S. H. Stares, Chem. Rev., vol. 93, p. 927–942 (1993), both of which are hereby included by reference. Among such anions are those formed from aluminum compounds such as those described in the immediately subsequent paragraph and $X^-$, including $R^{19}{}_3AlX^-$, $R^{19}{}_2AlClX^-$, $R^{19}AlCl_2X^-$, and $R^{19}AlOX^-$, wherein $R^{19}$ is alkyl. Other useful noncoordinating anions include $BAF^-$ {BAF=tetrakis [3,5-bis(trifluoromethyl)phenyl]borate}, $SbF_6{}^-$, $PF_6{}^-$, and $BF_4{}^-$, trifluoromethanesulfonate, p-toluenesulfonate, $(R_fSO_2)_2N^-$, and $(C_6F_5)_4B^-$.

By an alkyl aluminum compound is meant a compound in which at least one alkyl group is bound to an aluminum atom. Other groups such as alkoxide, oxygen, and halogen may also be bound to aluminum atoms in the compound.

By "hydrocarbylene" herein is meant a divalent group containing only carbon and hydrogen. Typical hydrocarbylene groups are —$(CH_2)_4$—, —$CH_2CH(CH_2CH_3)CH_2CH_2$— and

(IV)

If not otherwise stated, it is preferred that hydrocarbylene groups herein contain 1 to about 30 carbon atoms.

By "substituted hydrocarbylene" herein is meant a hydrocarbylene group which contains one or more substituent groups which are inert under the process conditions to which the compound containing these groups is subjected. The substituent groups also do not substantially interfere with the process. If not otherwise stated, it is preferred that substituted hydrocarbylene groups herein contain 1 to about 30 carbon atoms. Included within the meaning of "substituted" are heteroaromatic rings.

By a styrene herein is meant a compound of the formula

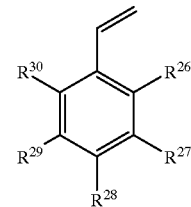

(V)

wherein $R^{26}$, $R^{27}$, $R^{26}$, $R^{29}$ and $R^{30}$ are each independently hydrogen, hydrocarbyl, substituted hydrocarbyl or a functional group, all of which are inert in the polymerization process. It is preferred that all of $R^{26}$, $R^{27}$, $R^{26}$, $R^{29}$ and $R^{30}$ are hydrogen.

By "a norbornene" is meant that the monomer is characterized by containing at least one norbornene-functional group in its structure including norbornadiene as identified by the formulas below, which can be substituted or unsubstituted

(VI)

wherein "a" represents a single or double bond. Representative monomers are compounds (VII) and (VIII) as follows:

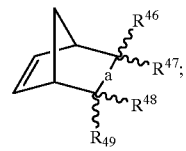

(VII)

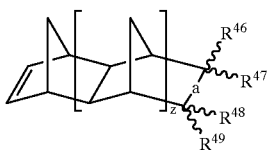

(VIII)

wherein $R^{46}$, $R^{47}$, $R^{48}$ and $R^{49}$ independently are hydrogen halogen, or hydrocarbyl, provided that, except if the hydrocarbyl group is vinyl, if any of the hydrocarbyl are alkenyl, there is no terminal double bond, i.e., the double bond is internal; or $R^{46}$ and $R^{48}$ taken together can be part of carbocyclic ring (saturated, unsaturated or aromatic); or $R^{46}$ and $R^{47}$ and/or $R^{48}$ and $R^{49}$ taken together are an alkylidene group. In these structures "z" is 1 to 5. Examples of such norbornenes include norbornadiene, 2-norbornene, 5-methyl-2-norbornene, 5-hexyl-2-norbornene, 5-ethylidene-2-norbornene, vinylnorbornene, dicyclopentadiene, dihydrodicyclopentadiene, tetracyclododecene, trimers of cyclopentadiene, halogenated norbornenes wherein $R^{46}$, $R^{47}$, $R^{48}$ and $R^{49}$ may also be halogen or fully halogenated alkyl groups such as $C_wF_{2w}+1$ wherein w is 1 to 20, such as perfluoromethyl and perfluorodecyl. The halogenated norbornenes can be synthesized via the Diels-Alder reaction of cyclopentadiene an appropriate dieneophile, such as $F_3CC\equiv CCF_3$ or $R^{49}{}_2C=CR^{49}C_wF_{2w}+1$ wherein each $R^{49}$ is independently hydrogen or fluorine and w is 1 to 20.

By "saturated hydrocarbyl" is meant a univalent group containing only carbon and hydrogen which contains no unsaturation, such as olefinic, acetylenic, or aromatic groups. Examples of such groups include alkyl and cycloalkyl. If not otherwise stated, it is preferred that saturated hydrocarbyl groups herein contain 1 to about 30 carbon atoms.

By "neutral Lewis base" is meant a compound, which is not an ion, which can act as a Lewis base. Examples of such compounds include ethers, amines, sulfides, and organic nitriles.

By "cationic Lewis acid" is meant a cation which can act as a Lewis acid. Examples of such cations are sodium and silver cations.

By "α-olefin" is meant a compound of the formula $CH_2=CHR^{14}$, wherein $R^{14}$ is n-alkyl or branched alkyl, preferably n-alkyl.

By "linear α-olefin" is meant a compound of the formula $CH_2=CHR^{14}$, wherein $R^{14}$ is n-alkyl. It is preferred that the linear α-olefin have 4 to 40 carbon atoms.

By an olefinic bond is meant a carbon-carbon double bond, but does not include bonds in aromatic rings.

By a rare earth metal is meant one of lanthanum, cerium, praseodymium, neodymium, promethium, samarium, europium, gadolinium, terbium, dysprosium, holmium, erbium, thulium, ytterbium or lutetium.

By a functional group is meant a group which does not interfere with the stability synthesis of, or functioning of a compound. Suitable functional groups may include (depending on which compound they are in) ether, halo, siloxy, silyl, ester, fluoroalkyl, fluorosulfonyl, and tertiary amino.

By a divalent organic moiety is meant a divalent group in which the free valences are to two different atoms in the group, and which contains at least one carbon atom. This moiety may contain one or more heteroatoms, preferably nitrogen or silicon. One or both of the free valencies may be to heteroatoms (as opposed to carbon atoms). Preferably both free valencies are to carbon atoms or nitrogen atoms, more preferably to carbon atoms.

By a silyl group is meant a group of the formula $-SiR^{16}R^{17}R^{18}$, wherein $R^{16}$, $R^{17}$ and $R^{18}$ are each independently hydrogen, hydrocarbyl, substituted hydrocarbyl, or a functional group.

The bis(carboximidamidatonates) can generally be made by the following method. A dialkali metal or alkaline earth metal salt is prepared, such as is shown in equation (1), from a suitable dihalogen compound or other suitable precursor. Such reactions to prepare these types of organometallic compounds are known in the art to prepare, for example, dilithium or dimagnesium compounds, see for instance G. Wilkinson, et al., Ed., Comprehensive Organometallic Chemistry, Pergamon Press, Oxford, 1982; J. Klein, et al., Tetrahedron, vol. 132, p. 51 (1976); and M. F. Lappert, et al., J. Chem. Soc. Chem. Commun, p. 14 (1982). The dialkali metal salt or alkaline earth metal salt is then reacted with 2 moles of a carbodiimide to form the corresponding alkali or alkaline earth metal salt of the bis(carboximidamidatonate), as shown in equation (2). The product of equation (2) is then reacted with a salt of an appropriate transition metal to form the transition metal complex of the bis(carboximidamidatonate) which may be used in the polymerization catalyst system. The use of a bis(carboximidamidatonate) (particularly the compound with a nontransition metal, such as an alkali metal or magnesium) to react with the salt of a transition metal is also novel, and preferably takes place in solution at a temperature of about −50°C. to about +100°C. By using appropriate groups or substituents on the various reactants, substituted bis(carboximidamidatonates) with different groups may be formed. Equations (1), (2) and (3) just illustrate one particular method of making these compounds.

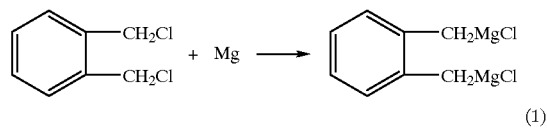

(1)

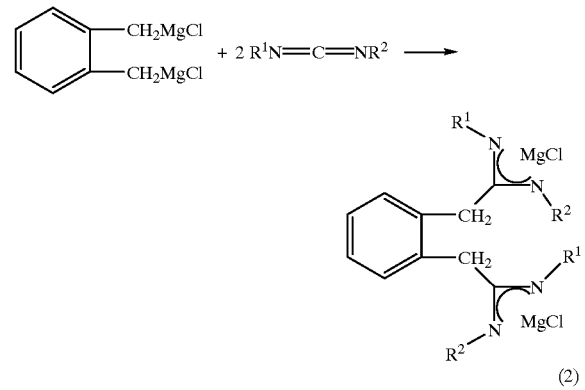

(2)

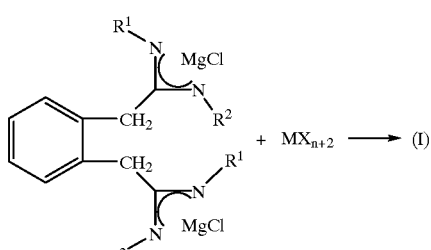 + MX$_{n+2}$ ⟶ (I)  (3)

In (X) and (XI) useful groups for $R^{15}$ include, for example, —CR$^{16}_2$(CR$^{16}_2)_q$CR$^{16}_2$— (XV), wherein each $R^{16}$ is independently hydrogen, hydrocarbyl or substituted hydrocarbyl and q is 0 or an integer from 1 to 20, especially q is 4. Other useful groups for $R^{15}$ include, for example, o-phenylene, 1,2-naphthylene, 2,3-naphthylene, 1,8-naphthylene, 1,2-cyclohexylene,

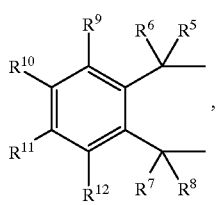 (XII)

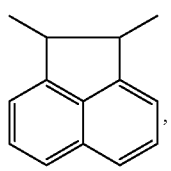 (XVI)

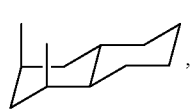 (XVII)

 (XVIII)

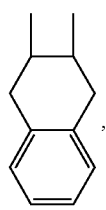 (IX)

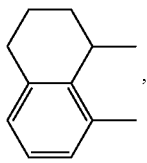 (XX)

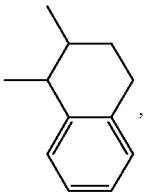 (XXI)

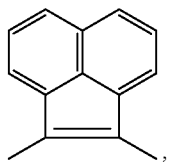 (XXII)

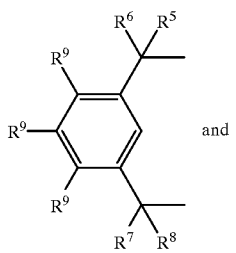 (XXIII)

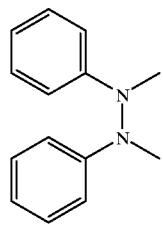 and (XXV)

wherein $R^5$, $R^6$, $R^7$ and $R^8$ are each independently hydrogen, hydrocarbyl or substituted hydrocarbyl, provided that either or both of the pairs $R^5$ and $R^6$, and $R^7$ and $R^8$ taken together may form a ring; and $R^9$, $R^{10}$, $R^{11}$ and $R^{12}$ are each independently hydrogen, hydrocarbyl, substituted hydrocarbyl, or a functional group, provided that any two of $R^9$, $R^{10}$, $R^{11}$ and $R^{12}$ vicinal to one another may form a ring. Preferred groups for $R^{15}$ are (XII), (XV) wherein q is 2 and/or each $R^{16}$ is hydrogen, (XV) in which q is 1, each $R^{16}$ on the terminal carbon atoms is hydrogen, and both $R^{16}$ groups on the middle carbon atom are methyl [—H$_2$CC(CH$_3$)$_2$CH$_2$—], and (XII), with (XV) being especially preferred. It is also preferred that $R^{15}$ contain at least two carbon atoms, and that each of the free valencies of $R^{15}$ are to different carbon atoms.

In another especially preferred embodiment of (X) and (XI), $R^{15}$ is (XII) or (XXIII) and the total compounds [when $R^{15}$ is (XII)] are of the formulas

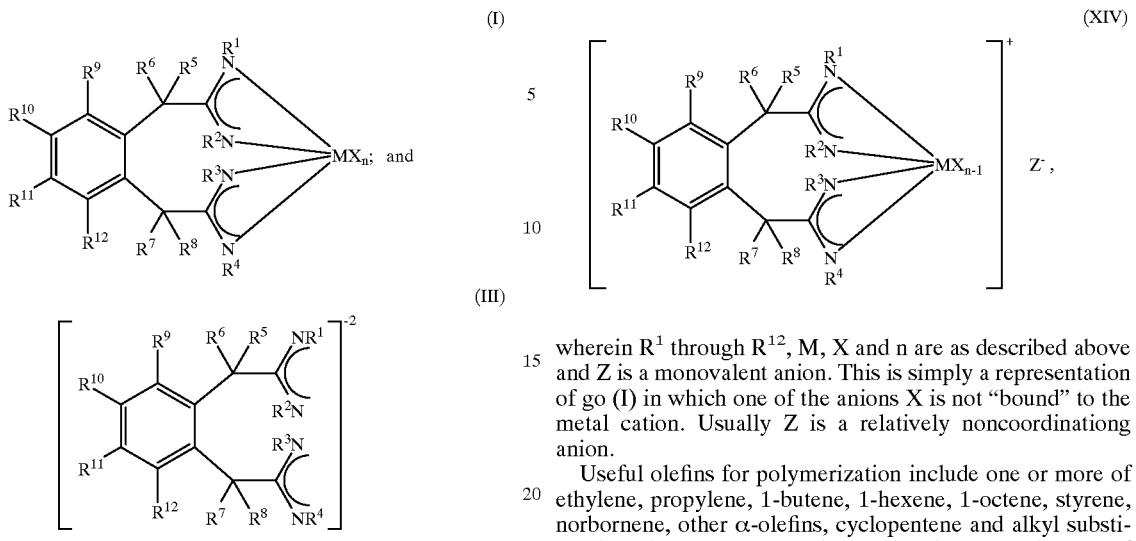

(I), (III), (XIV)

In (I), (III), (x), (xi), (XII), as appropriate it is preferred that:

$R^1$, $R^2$, $R^3$ and $R^4$ are each independently alkyl or silyl, more preferably alkyl containing 1 to 6 carbon atoms; and/or $R^1$, $R^2$, $R^3$ and $R^4$ are all the same; and/or $R^5$, $R^6$, $R^7$ and $R^8$ are each independently hydrogen or alkyl, more preferably all are hydrogen; and/or $R^9$, $R^{10}$, $R^{11}$ and $R^{12}$ are all hydrogen; and/or one or more of $R^9$, $R^{10}$, $R^{11}$ and $R^{12}$ are alkyl, aryl or substituted aryl.

In compounds such as (I) and (X) preferred transition metals are Zr, Ti, V and Hf, and Zr and Ti are more preferred. Preferred metal oxidation states are Ti[II, III, and IV], Zr[II and IV], Hf[IV], V[IV and V], Cr[III], Sc[III], Y[III] and the rare earth metals[III]. When lower oxidation states of the metals are employed, it may beneficial to include an oxidant in the catalyst activation step. This may be an alkyl halide to provide simultaneous alkylation if the compound is not prealkylated, or a standard oxidant such as oxygen when another alkylating agent is used. In compounds in which silyl groups are present it is preferred that $R^{16}$, $R^{17}$ and $R^{18}$ are each independently alkyl or aryl, more preferably alkyl, and especially preferably all are methyl.

Anions X may have one negative charge (monoanion), or more than one negative charge (dianion, etc.). The number of anions, X, which corresponds to n, can be a fractional number or a whole number, depending on the number of residual positive charges on the ligand plus metal cation. For example if the metal valence is 3, and the anion is a dianion ($X^{-2}$), then n would be 0.5. Preferred anions are monoanions. Useful anions include acyl, alkoxide, hydride, halide, carboxylate, alkyl such as methyl, benzyl, neopentyl, neophyl, and trimethylsilylmethyl, and preferred anions are halide, especially chloride and bromide, and alkyl.

Included within the meaning of a compound of formula (I) are compounds of the formula wherein $R^1$ through $R^{12}$, M, X and n are as described above and Z is a monovalent anion. This is simply a representation of go (I) in which one of the anions X is not "bound" to the metal cation. Usually Z is a relatively noncoordinationg anion.

Useful olefins for polymerization include one or more of ethylene, propylene, 1-butene, 1-hexene, 1-octene, styrene, norbornene, other α-olefins, cyclopentene and alkyl substituted cyclopentenes. Copolymers, such as copolymers of ethylene and one or more α-olefins may also be made. Preferred olefins are one or more of ethylene, propylene and is a linear α-olefin.

The second compound in the first polymerization process (and also useful in the second polymerization process), W, is a neutral Lewis acid that can abstract $X^-$ from (I) or (X) to form $WX^-$. Useful Lewis acids for this abstraction include $B(C_6F_5)_3$, $AlCl_3$, $MgCl_2$ and alkyl aluminum compounds such as methyl aluminoxane, diethylaluminum chloride and ethylaluminum chloride. If a hydrocarbyl anion, preferably an alkyl anion, more preferably a methyl anion, or a hydride anion, is not bound to the metal atom of (I), W (or another W) must also transfer a hydrocarbyl (preferably an alkyl) or hydride anion to the metal atom. Essentially the same effect can be obtained by using one molecule of the alkyl aluminum compound to place an alkyl group on the metal, and another molecule to abstract the X anion. Preferred neutral Lewis acids for transferring a hydrocarbyl group to the metal atom are alkyl aluminum compounds. Suitable alkyl aluminum compounds include alkyl aluminum sesquioxides [$(R^{18}AlO)n$], especially wherein $R^{18}$ is methyl. Alkyl aluminum sesquioxides are preferred alkyl aluminum compounds. W can also constitute a mixture of two compounds, a strong Lewis acid such as $B(C_6F_5)_3$ and an alkylating agent such as triethylaluminum. A stoichiometric or larger amount of the neutral Lewis acid is preferred, and a more preferred molar ratio of W:(I) is about 1 to about 10,000, preferably about 10 to about 5,000.

In the first and second polymerization processes herein, the temperature at which the polymerization is carried out is about –50° C. to about +250° C., preferably about –60° C. to about 150° C., more preferably about –20° C. to about 100° C. The pressure of the olefin (if it is a gas) at which the polymerization is carried out is not critical, atmospheric pressure to about 275 MPa being a suitable range.

The polymerization processes herein may be run in the presence of various liquids, particularly aprotic organic liquids. The catalyst system, olefin, and polymer may be soluble or insoluble in these liquids, but obviously these liquids should not prevent the polymerization from occurring. Suitable liquids include alkanes, cycloalkanes, selected halogenated hydrocarbons, and aromatic hydrocarbons. Specific useful solvents include hexane, toluene, benzene methylene chloride, and 1,2,4-trichlorobenzene.

The olefin polymerizations herein may also initially be carried out in the solid state by, for instance, supporting the transition metal compound on a substrate such as silica or alumina, activating it with the Lewis (such as W, for instance an alkylaluminum compound) or Bronsted acid and exposing it to the olefin. Alternatively, the support may first be contacted (reacted) with W such as an alkylaluminum compound, and then contacted with an appropriate transition metal compound such as (I) or (X). The support may also be able to take the place of the Lewis or Bronsted acid, for instance an acidic clay such as montmorillonite. Another method of making a supported catalyst is to start a polymerization or at least make a transition metal complex of another olefin or oligomer of an olefin such as cyclopentene on a support such as silica or alumina. These "heterogeneous" catalysts may be used to catalyze polymerization in the gas phase or the liquid phase. By gas phase is meant that a gaseous olefin is transported to contact with the catalyst particle.

In all of the polymerization processes described herein oligomers and polymers of the various olefins are made. They may range in molecular weight from oligomeric olefins, to lower molecular weight oils and waxes, to higher molecular weight polyolefins. One preferred product is a polymer with a degree of polymerization (DP) of about 10 or more, preferably about 40 or more. By "DP" is meant the average number of repeat (monomer) units in a polymer molecule.

Depending on its properties, the polymer made by the processes described herein is useful in many ways. For instance if it is a thermoplastic, it may be used as a molding resin, for extrusion, film, etc. If it is elastomeric, it may be used as an elastomer.

Polyolefins are most often prepared by polymerization processes in which a transition metal containing catalyst system is used. Depending on the process conditions used and the catalyst system chosen, polymers, even those made from the same monomer(s) may have varying properties. Some of the properties which may change are molecular weight and molecular weight distribution, crystallinity, melting point, and glass transition temperature. Except for molecular weight and molecular weight distribution, branching can affect all the other properties mentioned.

It is known that certain transition metal containing polymerization catalysts including those disclosed herein, are especially useful in varying the branching in polyolefins made with them, see for instance World Patent Applications 96/23010, 97/02298, 98/30609 and 98/30610. It is also known that blends of distinct polymers, that vary for instance in the properties listed above, may have advantageous properties compared to "single" polymers. For instance it is known that polymers with broad or bimodal molecular weight distributions may be melt processed (be shaped) more easily than narrower molecular weight distribution polymers. Similarly, thermoplastics such as crystalline polymers may often be toughened by blending with elastomeric polymers.

Therefore, methods of producing polymers which inherently produce polymer blends are useful especially if a later separate (and expensive) polymer mixing step can be avoided. However in such polymerizations one should be aware that two different catalysts may interfere with one another, or interact in such a way as to give a single polymer.

In such a process the catalysts disclosed herein can be termed the first active polymerization catalyst. Monomers useful with these catalysts are those described (and also preferred) above.

A second active polymerization catalyst (and optionally one or more others) is used in conjunction with the first active polymerization catalyst. The second active polymerization catalyst may be a late transition metal catalyst, for example as described in World Patent Applications 96/23010, 97/02298, 98/27124, 98/30609, 98/30610 and 98/30612. Other types of catalysts may also be used for the second active polymerization catalyst. For instance so-called Ziegler-Natta and/or metallocene-type catalysts may also be used. These types of catalysts are well known in the polyolefin field, see for instance Angew. Chem., Int. Ed. Engl., vol. 34, p. 1143–1170 (1995), European Patent Application 416,815 and U.S. Pat. No. 5,198,401 for information about metallocene-type catalysts, and J. Boor Jr., Ziegler-Natta Catalysts and Polymerizations, Academic Press, New York, 1979 for information about Ziegler-Natta-type catalysts, all of which are hereby included by reference. Many of the useful polymerization conditions for all of these types of catalysts and the first active polymerization catalysts coincide, so conditions for the polymerizations with (I) or (X) are easily accessible. Oftentimes the "co-catalyst" or "activator" is needed for metallocene or Ziegler-Natta-type polymerizations. In many instances the same compound, such as an alkylaluminum compound, may be used as an "activator" for some or all of these various polymerization catalysts.

In one preferred process described herein the first olefin(s) [the monomer(s) polymerized by the first active polymerization catalyst] and second olefin(s) [the monomer(s) polymerized by the second active polymerization catalyst] are identical, and preferred olefins in such a process are the same as described immediately above. The first and/or second olefins may also be a single olefin or a mixture of olefins to make a copolymer. Again it is preferred that they be identical particularly in a process in which polymerization by the first and second active polymerization catalysts make polymer simultaneously.

In some processes herein the first active polymerization catalyst may polymerize a monomer that may not be polymerized by said second active polymerization catalyst, and/or vice versa. In that instance two chemically distinct polymers may be produced. In another scenario two monomers would be present, with one polymerization catalyst producing a copolymer, and the other polymerization catalyst producing a homopolymer, or two copolymers may be produced which vary in the molar proportion or repeat units from the various monomers. Other analogous combinations will be evident to the artisan.

In another variation of this process one of the polymerization catalysts makes an oligomer of an olefin, preferably ethylene, which oligomer has the formula $R^{70}CH=CH_2$, wherein $R^{70}$ is n-alkyl, preferably with an even number of carbon atoms. The other polymerization catalyst in the process them (co)polymerizes this olefin, either by itself or preferably with at least one other olefin, preferably ethylene, to form a branched polyolefin. Preparation of the oligomer (which is sometimes called an α-olefin) by a second active polymerization-type of catalyst can be found in World Patent Applications 96/23010 and 98/30612.

Likewise, conditions for such polymerizations, using catalysts of the second active polymerization type, will also be found in the appropriate above mentioned references.

Two chemically different active polymerization catalysts are used in this polymerization process. The first active polymerization catalyst is described in detail above. The second active polymerization catalyst may also meet the limitations of the first active polymerization catalyst, but must be chemically distinct. For instance, it may have a different transition metal present, and/or utilize a different type of ligand and/or the same type of ligand which differs in structure between the first and second active polymerization catalysts. In one preferred process, the ligand type and the metal are the same, but the ligands differ in their substituents.

Included within the definition of two active polymerization catalysts are systems in which a single polymerization catalyst is added together with another ligand, preferably the same type of ligand, which can displace the original ligand coordinated to the metal of the original active polymerization catalyst, to produce in situ two different polymerization catalysts.

The molar ratio of the first active polymerization catalyst to the second active polymerization catalyst used will depend on the ratio of polymer from each catalyst desired, and the relative rate of polymerization of each catalyst under the process conditions. For instance, if one wanted to prepare a "toughened" thermoplastic polyethylene that contained 80% crystalline polyethylene and 20% rubbery polyethylene, and the rates of polymerization of the two catalysts were equal, then one would use a 4:1 molar ratio of the catalyst that gave crystalline polyethylene to the catalyst that gave rubbery polyethylene. More than two active polymerization catalysts may also be used if the desired product is to contain more than two different types of polymer.

The polymers made by the first active polymerization catalyst and the second active polymerization catalyst may be made in sequence, i.e., a polymerization with one (either first or second) of the catalysts followed by a polymerization with the other catalyst, as by using two polymerization vessels in series. However it is preferred to carry out the polymerization using the first and second active polymerization catalysts in the same vessel(s), i.e., simultaneously. This is possible because in most instances the first and second active polymerization catalysts are compatible with each other, and they produce their distinctive polymers in the other catalyst's presence. Any of the processes applicable to the individual catalysts may be used in this polymerization process with 2 or more catalysts, i.e., gas phase, liquid phase, continuous, etc.

The polymers produced by this process may vary in molecular weight and/or molecular weight distribution and/or melting point and/or level of crystallinity, and/or glass transition temperature and/or other factors. For copolymers the polymers may differ in ratios of comonomers if the different polymerization catalysts polymerize the monomers present at different relative rates. The polymers produced are useful as molding and extrusion resins and in films as for packaging. They may have advantages such as improved melt processing, toughness and improved low temperature properties.

Hydrogen may be used to lower the molecular weight of polyolefin produced in the first or second processes. It is preferred that the amount of hydrogen present be about 0.01 to about 50 mole percent of the olefin present, preferably about 1 to about 20 mole percent. When liquid monomers (olefins) are present, one may need to experiment briefly to find the relative amounts of liquid monomers and hydrogen (as a gas). If both the hydrogen and monomer(s) are gaseous, their relative concentrations may be regulated by their partial pressures.

In the Examples, the following abbreviations are used:
$\Delta H_f$—heat of fusion (of polymer)
Cy—cyclohexyl
GPC—Gel Permeation Chromatography
MI—melt index
Mn—number average molecular weight
Mw—weight average molecular weight
PE—polyethylene
PMAO—poly(methylaluminoxane)
PMAO-IP—see PMAO
PP—polypropylene
Pr—propyl
RT—room temperature
THF—tetrahydrofuran In the Examples, all pressures are gauge pressures.

"Me/1000 $CH_2$" is the total number of methyl groups per 1000 methylene groups in the polymer and is measured by $^1$H NMR. For method of NMR measurement and calculations, see World Patent Application 96/23010.

Differential Scanning Calorimetry was used to measure polymer melting points (Tm in ° C., taken as the peak of the melting endotherm), and heat of fusion ($\Delta H_f$ in J/g), using a heating rate of 10° C./min. Results reported are from the second heat.

The dimagnesium reagents were prepared according to the procedure of M. F. Lappert and T. R. Martin, J. Chem. Soc. Dalton Trans. 1982, 1959. Excess magnesium metal was reacted with dichloro- or dibromo-hydrocarbon compounds in THF at RT to yield a high yield of the dimagnesium reagents which were then reacted with 1 equiv of the carbodiimide in THF at RT for 2–3 days. The solvent was removed in vacuo and the crude products were washed with pentane to give a white powder product.

EXAMPLE 1

Synthesis of [MgCl]$_2$[(i—PrN)$_2$CCH$_2$C$_6$H$_4$—o—CH$_2$C(NPr—i)$_2$]

In a dry-box, to a solution of [MgCl]$_2$[CH$_2$C$_6$H$_4$—o—CH$_2$] (0.0164 mol) in THF at –300° C. was added dropwise a solution of 1,3-diisopropylcarbodiimide (4.139 g, 0.0327 mol) in THF. The pale yellow reaction mixture was stirred 2 days. The solvent was removed in vacuo and the white sticky crude product was washed with pentane to give a white powder product (5.1558 g, 0.0108 mol) in 66% yield. $^1$H NMR (CD$_2$Cl$_2$): 1.31 (m, 24H, CH$_3$), 3.1 (s, 4H, CH$_2$), 3.58 (m, 4H, i—Pr—CH), 7.22 (m, 2H, Ar—H), 7.58 (m, 2H, Ar—H).

EXAMPLE 2

Synthesis of [MgCl]$_2$[(NC$_6$H$_{11}$)$_2$CCH$_2$C$_6$H$_4$—o—CH$_2$C(NC$_6$H$_{11}$)$_2$]

In a dry-box, to a solution of [MgCl]$_2$[CH$_2$C$_6$H$_4$—o—CH$_2$] (0.0169 mol) in THF at –30° C. was added dropwise a solution of 1,3-dicyclohexylcarbodiimide (6.971 g, 0.0338 mol) in THF. The pale yellow reaction mixture was stirred 3 days. The solvent was removed in vacuo and the white sticky crude product was washed with pentane to give a white powder product (7.698 g, 0.0121 mol) in 72% yield. $^1$H NMR (CD$_2$Cl$_2$): broad, 1.0–1.8 (m, 20H, Cy—CH$_2$), 3.0 (m, 4H, Cy—CH), 3.69 (br, 2H, CH$_2$), 3.78 (br, 2H, CH$_2$), 7.2 (m, Ar—H).

EXAMPLE 3

Synthesis of [MgBr]$_2$[(i—PrN)$_2$CCH$_2$CH$_2$CH$_2$CH$_2$C(NPr—i)$_2$]

The general procedure was followed using 11.25 mmol of [MgBr]$_2$[CH$_2$CH$_2$CH$_2$CH$_2$] and 2.8395 g (22.5 mmol) of 1,3-diisopropylcarbodiimide. A white powder product (6.3672 g, 8.72 mmol) was isolated in 78% yield. $^1$H NMR (CD$_2$Cl$_2$): 1.08 (d, 24H, CH$_3$), 1.57 (br, 4H, CH$_2$), 1.90 (m, THF coordinated CH$_2$), 2.29 (br, 4H, CH$_2$), 3.54 (br, 4H, CH), 3.80 (m, THF coordinated OCH$_2$).

EXAMPLE 4

Synthesis of [MgBr]$_2$[(ArN)$_2$CCH$_2$CH$_2$CH$_2$CH$_2$C(NAr)$_2$]: [Ar=2,6-(i—Pr)$_2$C$_6$H$_3$]

The general procedure was followed using 15.6 mmol of [MgBr]$_2$[CH$_2$CH$_2$CH$_2$CH$_2$] and 11.3354 g (31.2 mmol) of 1,3-bis[2,6-diisopropylphenyl]carbodiimide. A white powder product (15.9027 g, 12.1 mmol) was isolated in 78% yield. $^1$H NMR (CD$_2$Cl$_2$): 0.35 (br, 4H, CH$_2$), 0.86 (d, 24H, CH$_3$), 0.96 (d, 24H, CH$_3$), 1.19 (br, 4H, CH$_2$), 1.70 (m, THF coordinated CH$_2$), 3.08 (br, 8H, CH), 3.70 (m, THF coordinated OCH$_2$), 6.83 (m, 12H, Ar—H).

EXAMPLE 5

Synthesis of [MgCl]$_2$[(ArN)$_2$CCH$_2$(C$_6$H$_4$)—m—CH$_2$C(NAr)$_2$]: [Ar=2,6-(i—Pr)$_2$C$_6$H$_3$]

The general procedure was followed using 37.0 mmol of [MgCl]$_2$[CH$_2$C$_6$H$_4$—m—CH$_2$] and 26.8294 g (74.0 mmol) of 1,3-bis[2,6-diisopropylphenyl]carbodiimide. A pale yellow powder product (36.34 g, 28.26 mmol) was isolated in 76% yield. $^1$H NMR (CD$_2$Cl$_2$): 0.35 (br, 4H, CH$_2$), 0.86 (d, 24H, CH$_3$), 0.96 (d, 24H, CH$_3$), 1.19 (br, 4H, CH$_2$), 1.70 (m, THF coordinated CH$_2$), 3.08 (br, 8H, CH), 3.70 (m, THF coordinated OCH$_2$), 6.83 (m, 12H, Ar—H).

EXAMPLE 6

Synthesis of [MgCl]$_2$[(i—PrN)$_2$CCH$_2$(C$_6$H$_4$)—m—CH$_2$C(NPr—i)$_2$]

The general procedure was followed using 14.7 mmol of [MgCl]$_2$[CH$_2$C$_6$H$_4$—m—CH$_2$] and 3.7021 g (29.34 mmol) of 1,3-diisopropylcarbodiimide. A white powder product (4.675 g, 7.37 mmol) was isolated in 50% yield. $^1$H NMR (CD$_2$Cl$_2$): 0.79 (d, 24H, CH$_3$), 1.73 (m, 4H, THF coordinated CH$_2$), 3.2 (m, 4H, CH), 3.48 (s, 4H, CH$_2$), 3.82 (m, 4H, THF coordinated OCH$_2$), 6.85 (m, 2H, Ar—H), 6.96 (m, 2H, Ar—H).

EXAMPLE 7

Synthesis of [MgBr]$_2$[(ArN)$_2$CCH$_2$CH$_2$CH$_2$CH$_2$C(NAr)$_2$]: [Ar=4-Me—C$_6$H$_4$]

The general procedure was followed using 9.42 mmol of [MgBr]$_2$[CH$_2$CH$_2$CH$_2$CH$_2$] and 4.19 g (18.85 mmol) of 1,3-bis[4-methylphenyl]carbodiimide. A white powder product (7.4264 g, 7.57 mmol) was isolated in 80% yield. $^1$H NMR (CD$_2$Cl$_2$): 1.20 (br, 2×CH$_2$ and THF overlap), 2.21 (s, 12H, CH$_3$), 2.32 (br, 4H, CH$_2$), 3.70 (br, THF coordinated OCH$_2$), 6.65–7.22 (m, 16H, Ar—H).

EXAMPLE 8

Synthesis of [MgCl]$_2$[(ArN)$_2$CCH$_2$(C$_6$H$_4$)—m—CH$_2$C(NAr)$_2$]: [Ar=4-Me—C$_6$H$_4$]

The general procedure was followed using 9.17 mmol of [MgCl]$_2$[CH$_2$C$_6$H$_4$—m—CH$_2$] and 4.077 g (18.34 mmol) of 1,3-bis[4-methylphenyl]carbodiimide. A pale yellow powder product (7.0 g, 7.16 mmol) was isolated in 78% yield. $^1$H NMR (CD$_2$Cl$_2$): 1.28 (br, THF—CH$_2$), 2.22 (s, 12H, CH$_3$), 3.70 (br, THF coordinated OCH$_2$), 4.05 (s, 4H, CH$_2$), 6.65–7.15 (m, 16H, Ar—H).

General Procedure for Synthesis of Transition Metal Complexes of Bis-(carboximidatonate)

A flask containing a suspension of metal halide in pentane or methylene chloride or toluene was cooled at −30° C. in the dry-box freezer. To this was added dropwise a pre-cooled solution of bis-(carboximidatonate) dimagnesium reagent in CH$_2$Cl$_2$. The reaction mixture was stirred overnight at RT and filtered through a frit with dry Celite. The solvent was removed under vacuo and the residue was extracted with methylene chloride. Removed methylene chloride and washed with pentane and then dried in vacuo to give the early-transition metal complexes. The formulas below list the catalysts synthesized in these examples.

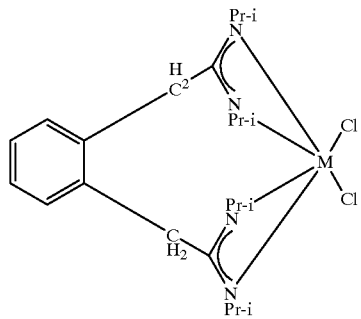

1: M = Ti,
2: M = Zr,
3: M = Hf.

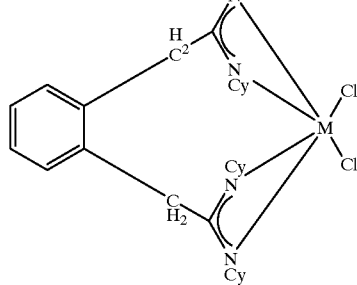

4: M = Ti,
5: M = Zr,
6: M = Hf.

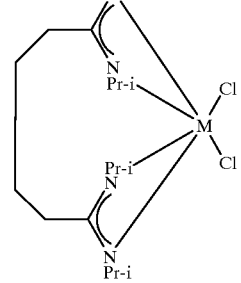

7: M = Ti,
8: M = Zr,
9: M = Hf.

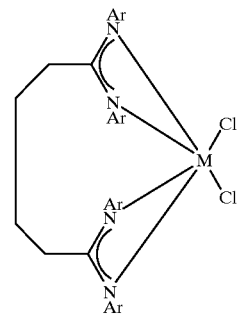

Ar = 2,6-i-Pr——C$_6$H$_4$
10: M = Ti,
11: M = Zr,
12: M = Hf,
13: M = V (III)*,
14: M = Y*,
15: M = Cr (III)*.

Ar = 4-Me——C$_6$H$_4$
21: M = Ti,
22: M = Zr.

-continued

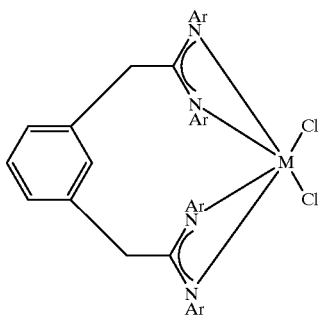

Ar = 2,6-i-Pr—C₆H₄
16: M = Ti,
17: M = Zr,
18: M = Hf.

Ar = 4-Me—C₆H₄
23: M = Ti,
24: M = Zr.

* One Cl atom on the metal.

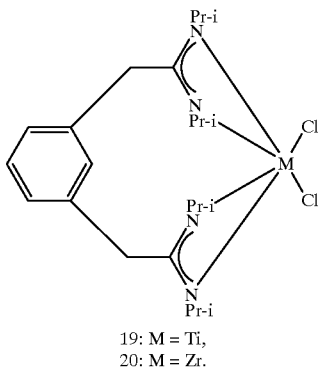

19: M = Ti,
20: M = Zr.

EXAMPLE 9

Synthesis of [(i—PrN)$_2$CCH$_2$C$_6$H$_4$—o—CH$_2$C(NPr—i)$_2$]TiCl$_2$: 1

In a dry-box, a solution of [MgCl]$_2$[(i—PrN)$_2$CCH$_2$C$_6$H$_4$—o—CH$_2$C(NPr—i)$_2$] (1.299 mmol) in toluene (14 mL) and THF (1 mL) was added dropwise to a pre-cooled solution of TiCl$_4$ (0.2464 g, 1.299 mmol) in toluene at −30° C. The purple reaction mixture was stirred 2 days and the solvent was removed in vacuo. The residue was extracted with methylene chloride. After removal of the solvent, a dark purple powder was obtained, 0.5215 g (1.097 mmol) in 84% yield. $^1$H NMR (CD$_2$Cl$_2$): contain different isomers. 1.06–1.30 (br., m, 24H, CH$_3$), 2.62–2.96 (s, 4H, CH$_2$), 3.26–3.72 (m, 4H, i—Pr—CH), 6.86–7.30 (br., m, 4H, Ar—H).

EXAMPLE 10

Synthesis of [(i—PrN)$_2$CCH$_2$C$_6$H$_4$—o—CH$_2$C(NPr—i)$_2$]ZrCl$_2$: 2

In a dry-box, a solution of [MgCl]$_2$[(i—PrN)$_2$CCH$_2$C$_6$H$_4$—o—CH$_2$C(NPr—i)$_2$] (0.7716 mmol) in toluene (14 mL) and THF (1 mL) was dropwise added a pre-cooled suspension of ZrCl$_4$ (0.1798 g, 0.7716 mmol) in toluene at −30° C. The cloudy pale yellow reaction mixture was stirred 2 days and the solvent was removed in vacuo. The residue was extracted with methylene chloride. After removal of the solvent, a pale yellow powder was obtained, 0.1963 g (0.378 mmol) in 49% yield. $^1$H NMR (CD$_2$Cl$_2$): contain different isomers. 0.96–1.35 (br., m, 24H, CH$_3$), 2.62–3.04 (s, 4H, CH$_2$), 3.18–3.78 (m, 4H, i—Pr—CH), 6.80–7.40 (br., m, 4H, Ar—H).

EXAMPLE 11

Synthesis of [(i—PrN)$_2$CCH$_2$C$_6$H$_4$—o—CH$_2$C(NPr—i)$_2$]HfCl$_2$: 3

The general procedure for metal complexes was followed using 0.3943 g (0.835 mmol) of the dimagnesium reagent and 0.2673 g (0.835 mmol) of HfCl$_4$ and methylene chloride as solvent. A pale yellow solid (0.3002 g, 0.495 mmol) was obtained in 59% yield. $^1$H NMR spectrum in CD$_2$Cl$_2$ is complex and similar to the Zr analog compound.

EXAMPLE 12

Synthesis of [(NC$_6$H$_{11}$)$_2$CCH$_2$C$_6$H$_4$—o—CH$_2$C(NC$_6$H$_{11}$)$_2$]TiCl$_2$: 4

The general procedure for metal complexes was followed using 0.7168 g (1.126 mmol) of the dimagnesium reagent and 0.2137 g (1.126 mmol) of TiCl$_4$. A purple solid (0.4335 g, 0.682 mmol) was obtained in 61% yield. The $^1$H NMR spectrum in CD$_2$Cl$_2$ is complex.

EXAMPLE 13

Synthesis of [(NC$_6$H$_{11}$)$_2$CCH$_2$C$_6$H$_4$—o—CH$_2$C(NC$_6$H$_{11}$)$_2$]ZrCl$_2$: 5

The general procedure for metal complexes was followed using 0.6267g (0.9848 mmol) of the dimagnesium reagent and 0.2295 g (0.9848 mmol) of ZrCl$_4$. A pale yellow solid (0.2817 g, 0.415 mmol) was obtained in 42% yield. The $^1$H NMR spectrum in CD$_2$Cl$_2$ is complex.

EXAMPLE 14

Synthesis of [(NC$_6$H$_{11}$)$_2$CCH$_2$C$_6$H$_4$—o—CH$_2$C(NC$_6$H$_{11}$)$_2$]HfCl$_2$: 6

The general procedure for metal complexes was followed using 0.4603g (0.723 mmol) of the dimagnesium reagent and 0.2317 g (0.723 mmol) of ZrCl$_4$. A pale yellow solid (0.4742 g, 0.619 mmol) was obtained in 86% yield. The $^1$H NMR spectrum in CD$_2$Cl$_2$ is complex and similar to the Zr analog compound.

EXAMPLE 15

Synthesis of [(i—PrN)$_2$CCH$_2$CH$_2$CH$_2$CH$_2$C(NPr—i)$_2$]TiCl$_2$: 7

The general procedure for metal complexes was followed using 0.8054g (1.104 mmol) of the dimagnesium reagent and 0.2094 g (1.104 mmol) of TiCl$_4$. A dark red solid (0.6485 g, 0.906 mmol) was obtained in 82% yield. The $^1$H NMR spectrum in CD$_2$Cl$_2$ is complex and similar to the Zr analog compound.

EXAMPLE 16

Synthesis of [(i—PrN)$_2$CCH$_2$CH$_2$CH$_2$CH$_2$C(NPr—i)$_2$]ZrCl$_2$: 8

The general procedure for metal complexes was followed using 0.7443 g (1.02 mmol) of the dimagnesium reagent and 0.2377 g (1.02 mmol) of ZrCl$_4$. A pale yellow solid (0.5660 g, 0.735 mmol) was obtained in 72% yield. $^1$H NMR (CD$_2$Cl$_2$) 1.25 (br., m, 24H, CH$_3$), 1.58 (s, 4H, CH$_2$), 1.87 (m, 4H, THF—CH2), 2.38 (s, 4H, CH$_2$), 3.60 (m, 4H, i—Pr—CH), 3.94 (m, 4H, OCH$_2$).

EXAMPLE 17

Synthesis of [(i—PrN)$_2$CCH$_2$CH$_2$CH$_2$CH$_2$C(NPr—i)$_2$]HfCl$_2$: 9

The general procedure for metal complexes was followed using 0.4647g (0.6369 mmol) of the dimagnesium reagent and 0.2040 g (0.6369 mmol) of HfCl$_4$. A pale yellow solid (0.15 g, 0.269 mmol) was obtained in 42% yield. $^1$H NMR (CD$_2$Cl$_2$) 1.21 (br., m, 24H, CH$_3$), 1.60 (s, 4H, CH$_2$), 1.92 (m, 4H, THF—CH$_2$), 2.40 (s, 4H, CH$_2$), 3.78 (m, 4H, i—Pr—CH), 4.0 (m, 4H, OCH$_2$).

EXAMPLE 18

Synthesis of {[N(2,6-i—Pr$_2$—C$_6$H$_3$)]$_2$CCH$_2$CH$_2$CH$_2$CH$_2$C[N(2,6-i—Pr$_2$—C$_6$H$_3$)]2}TiCl$_2$: 10

The general procedure for metal complexes was followed using 2.6268 g (2.0 mmol) of the dimagnesium reagent and 0.3792 g (2.0 mmol) of TiCl$_4$. A red solid (2.1 g, 2.0 mmol) was obtained in ~100% yield. $^1$H NMR (CD$_2$Cl$_2$): 0.75–1.35 (m, overlap peaks, 56H, CH$_2$ and CH$_3$), 1.80 (m, THF coordinated CH$_2$), 2.92 (br, 2H, CH), 2.98 (br, 4H, CH), 3.14 (br, 2H, CH), 3.88 (m, THF coordinated OCH$_2$), 6.75–7.30 (m, 12H, Ar—H).

EXAMPLE 19

Synthesis of {[N(2,6-i—Pr$_2$—C$_6$H$_3$)]$_2$CCH$_2$CH$_2$CH$_2$CH$_2$C[N(2,6-i—Pr$_2$—C$_6$H$_3$)]$_2$}ZrCl$_2$: 11

The general procedure for metal complexes was followed using 2.7864 g (2.12 mmol) of the dimagnesium reagent and 0.4941 g (2.12 mmol) of ZrCl$_4$. An off-white solid (1.45 g, 1.54 mmol) was obtained in 73% yield. $^1$H NMR (CD$_2$Cl$_2$): 1.08 (d, 12H, CH$_3$), 1.15 (d, 12H, CH$_3$), 1.33 (d, 12H, CH$_3$), 1.40 (d, 12H, CH$_3$), 1.25 (br, 4H, CH$_2$), 1.92 (br, 4H, CH$_2$), 1.92 (m, THF coordinated CH$_2$), 2.75 (br, 4H, CH), 3.04 (br, 4H, CH), 3.94 (m, THF coordinated OCH$_2$), 6.90–7.68 (m, 12H, Ar—H).

EXAMPLE 20

Synthesis of {[N(2,6-i—Pr$_2$—C$_6$H$_3$ )]$_2$ CCH$_2$CH$_2$CH$_2$C[N(2, 6-i—Pr$_2$—C$_6$H$_3$)]$_2$}HfCl$_2$: 12

The general procedure for metal complexes was followed using 2.3058 g (1.75 mmol) of the dimagnesium reagent and 0.5620 g (1.75 mmol) of HfCl$_4$. An off-white solid (1.60 g, 1.55 mmol) was obtained in 89% yield. $^1$H NMR (CD$_2$Cl$_2$): 0.32 (br, 4H, CH$_2$), 0.84 (d, 24H, CH$_3$), 0.98 (d, 24H, CH$_3$), 1.82 (m, THF coordinated CH$_2$), 1.92 (br, 4H, CH$_2$), 2.88 (br, 4H, CH), 3.08 (br, 4H, CH), 3.88 (m, THF coordinated OCH$_2$), 6.72–7.20 (m, 12H, Ar—H).

EXAMPLE 21

Synthesis of {[N(2,6-i—Pr$_2$—C$_6$H$_3$)]$_2$CCH$_2$CH$_2$CH$_2$ CH$_2$C[N(2,6-i—Pr$_2$—C$_6$H$_3$)]2}VCl: 13

The general procedure for metal complexes was followed using 0.3910 g (0.3 mmol) of the dimagnesium reagent and 0.0468 g (0.3 mmol) of VCl$_3$. A purple solid which is not soluble in any organic solvents was received.

EXAMPLE 22

Synthesis of {[N(2,6-i—Pr$_2$—C$_6$H$_3$)]$_2$CCH$_2$CH$_2$CH$_2$CH$_2$C[N(2,6-i—Pr$_2$—C$_6$H$_3$)]$_2$}YCl: 14

The general procedure for metal complexes was followed using 0.5633 g (0.43 mmol) of the dimagnesium reagent and 0.0837 g (0.43 mmol) of YCl$_3$. An off-white solid (0.4 g, 0.41 TV5 mmol) was obtained in 94% yield. $^1$H NMR (CD$_2$Cl$_2$): complex.

EXAMPLE 23

Synthesis of {[N(2,6-i—Pr$_2$—C$_6$H$_3$)]$_2$CCH$_2$CH$_2$CH$_2$CH$_2$C[N(2,6-i—Pr$_2$—C$_6$H$_3$)]$_2$}CrCl: 15

The general procedure for metal complexes was followed using 0.2939 g (0.22 mmol) of the dimagnesium reagent and 0.0838 g (0.22 mmol) of CrCl$_3$ 3THF. A pale green solid was obtained. $^1$H NMR (CD$_2$Cl$_2$): 1.08 (d, 12H, CH$_3$), 1.28 (d, 12H, CH$_3$), 1.50 (m, 24H, CH$_3$), 2.15 (br, 4H, CH$_2$), 2.22 (br, 4H, CH$_2$), 3.36 (m, 4H, CH), 3.46 (br, 4H, CH), 6.92–7.45 (m, 12H, Ar—H).

EXAMPLE 24

Synthesis of {[N(2,6-i—Pr$_2$—C$_6$H$_3$)]$_2$CCH$_2$C$_6$H$_4$—m—CH$_2$C[N(2,6-i—Pr$_2$—C$_6$H$_3$)]$_2$}TiCl$_2$: 16

The general procedure for metal complexes was followed using 1.5927 g (1.239 mmol) of the dimagnesium reagent and 0.2350 g (1.24 mmol) of TiCl$_4$. A red brown solid (1.18 g, 1.2 mmol) was obtained in 97% yield. $^1$H NMR (CD$_2$Cl$_2$): complex and contained different isomers.

EXAMPLE 25

Synthesis of {[N(2,6-i—Pr$_2$—C$_6$H$_3$)]$_2$CCH$_2$C$_6$H$_4$—m—CH$_2$C[N(2,6-i—Pr$_2$—C$_6$H$_3$)]$_2$}ZrCl$_2$: 17

The general procedure for metal complexes was followed using 1.3342 g (1.038 mmol) of the dimagnesium reagent and 0.2418 g (1.038 mmol) of ZrCl$_4$. A pale yellow solid (1.05 g, 1.1 mmol) was obtained in ~100% yield. $^1$H NMR (CD$_2$Cl$_2$): complex and contained different isomers.

EXAMPLE 26

Synthesis of {[N(2,6-i—Pr$_2$—C$_6$H$_3$)]$_2$CCH$_2$C$_6$H$_4$—m—CH$_2$C[N(2,6-i—Pr$_2$—C$_6$H$_3$)]$_2$}HfCl$_2$: 18

The general procedure for metal complexes was followed using 1.4227 g (1.106 mmol) of the dimagnesium reagent and 0.3544 g (1.106 mmol) of HfCl$_4$. A pale yellow solid (0.9741 g) was obtained. The pale yellow solid was extracted with pentane. The pentane solution was concentrated and cooled in the freezer to yield colorless crystals which was identified as neutral ligand (identified by x-ray crystal structure). It is believed that trace of HCl contaminated in HfCl$_4$ reacted with the dimagnesium reagent to form the neutral ligand as a low-level byproduct.

EXAMPLE 27

Synthesis of [N(i—Pr)]$_2$CCH$_2$C$_6$H$_4$—m—CH$_2$C[N(i—Pr)]$_2$}TiCl$_2$: 19

At −30° C. in the dry-box, to a solution of 0.2805 g (0.84 mmol) of TiCl$_4$(THF)$_2$ in 30 mL of toluene, was slowly added a solution 0.84 mmol of the dimagnesium reagent in 20 mL of toluene. The dark red reaction mixture was stirred overnight at RT and filtered through a Celite® plug frit. After removing the solvent and rinsing with pentane, a dark red solid was obtained, 0.21 g, 0.44 mmol in 53% yield. $^1$H NMR (CD$_2$Cl$_2$): 1.4 (br, 24H, CH$_3$), 3.92 (br, 8H, CH$_2$ and CH—Pr—i), 7.12–7.4 (m, 4H, Ar—H).

EXAMPLE 28

Synthesis of [N(i—Pr)]$_2$CCH$_2$C$_6$H$_4$—m—CH$_2$C[N(i—Pr)]$_2$}ZrCl$_2$: 20

At −30° C., in a dry-box, to a solution of 0.3169 g (0.84 mmol) of ZrCl$_4$(THF)$_2$ in 30 mL of toluene was slowly added a solution of 0.84 mmol of the dimagnesium reagent in 20 mL of toluene. The cloudy reaction mixture was stirred overnight at RT and filtered through a Celite plug frit. After removing the solvent and rinsing with pentane, a pale yellow solid was obtained, 0.34 g, 0.65 mmol in 78% yield. $^1$H NMR (CD$_2$Cl$_2$): 1.42 (br, 24H, CH$_3$), 3.88 (br, 4H, CH—Pr—i), 4.05 (s, 4H, CH$_2$), 7.25–7.54 (m, 4H, Ar—H).

EXAMPLE 29

Synthesis of {[N(4-Me—C$_6$H$_4$)]$_2$CCH$_2$CH$_2$CH$_2$CH$_2$C[N(4-Me—C$_6$H$_4$)]$_2$}TiCl$_2$: 21

At −30° C., in a dry-box to a solution of 0.1564 g (0.47 mmol) of TiCl$_4$(THF)$_2$ in 30 mL of toluene, was slowly added a solution of 0.47 mmol of the dimagnesium reagent in 20 mL of toluene. The red reaction mixture was stirred overnight at RT and filtered through a Celite® plug frit. After removing the solvent and rinsing with pentane, a red solid was obtained, 0.33 g, 0.53mmol in ~100% yield. $^1$H NMR (CD$_2$Cl$_2$): contains toluene and coordinate THF. 0.53 (br, 4H, CH$_2$), 1.58 (s, 4H, CH$_2$), 1.72 (br, THF—CH$_2$), 2.18 (br, 12H, CH$_3$), 3.78 (br, THF—OCH$_2$), 6.31–7.12 (m, 16H, Ar—H).

EXAMPLE 30

{[N(4-Me—C$_6$H$_4$)]$_2$CCH$_2$CH$_2$CH$_2$CH$_2$C[N(4-Me—C$_6$H$_4$)]$_2$}ZrCl$_2$: 22

At −30° C., in the dry-box, to a solution of 0.3791 g (1.63 mmol) of ZrCl$_4$(THF)$_2$ in 30 mL of toluene, was slowly added a solution of 1.63 mmol of the dimagnesium reagent in 20 mL of toluene. The pale yellow cloudy reaction mixture was stirred overnight at RT and filtered through a Celite plug frit. After removing the solvent and rinsing with pentane, a pale yellow solid was obtained, 1.06 g, 1.60 mmol in 98% yield. $^1$H NMR (CD$_2$Cl$_2$): 0.60 (br, 4H, CH$_2$), 0.98 (br, 4H, CH$_2$), 1.36 (br, THF—CH$_2$), 2.20 (br, 12H, CH$_3$), 3.80 (br, THF—OCH$_2$), 6.08–6.95 (br, 16H, Ar—H).

EXAMPLE 31

Synthesis of {[N(4-Me—C$_6$H$_4$)]$_2$CCH$_2$C$_6$H$_4$-m—CH$_2$C[N(4-Me—C$_6$H$_4$)]$_2$}TiCl$_2$: 23

At −30° C., in the dry-box, to a solution of 0.1534 g (0.46 mmol) of TiCl$_4$(THF)$_2$ in 30 mL of toluene, was slowly added a solution of 0.4491 g (0.46 mmol) of the dimagnesium reagent in 20 mL of toluene. The red reaction mixture was stirred overnight at RT and filtered through a Celite plug frit. After removing the solvent and rinsing with pentane, a dark red solid was obtained, 0.30 g, 0.45 mmol in 98% yield. $^1$H NMR (CD$_2$Cl$_2$): contains toluene. 1.96 (br, 12H, CH$_3$), 3.15 (br, 4H, CH$_2$), 6.64–7.00 (m, 20H, Ar—H)

EXAMPLE 32

Synthesis of {[N(4-Me—C$_6$H$_4$)]$_2$CCH$_2$C$_6$H$_4$-m—CH$_2$C[N(4-Me—C$_6$H$_4$)]$_2$}ZrCl$_2$: 24

At −30° C., in the dry-box, to a solution of 0.2417 g (1.037 mmol) of ZrCl$_4$(THF)$_2$ in 30 mL of toluene, was slowly added a solution of 1.014 g (1.037 mmol) of the dimagnesium reagent in 20 mL of toluene. The pale yellow cloudy reaction mixture was stirred overnight at RT and filtered through a Celite plug frit. After removing the solvent and rinsing with pentane, a pale yellow solid was obtained, 0.6 g, 0.84 mmol in 81% yield. $^1$H NMR (CD$_2$Cl$_2$): contains toluene. 1.7 (br, THF—CH$_2$), 2.15 (br, 12H, CH$_3$), 3.70 (br, THF—OCH$_2$), 3.88 (br, 4H, CH$_2$), 6.24–7.00 (m, 20H, Ar—H).

EXAMPLES 33–45

Polymerization of Ethylene at About 35 kPa

Method A: In a dry-box, 0.02 mmol of the bis (carboximidatonate) transition metal catalyst was placed in a Schlenk flask and 35 mL of toluene was added to dissolve or partially dissolve the catalyst. The flask was sealed, removed from the dry-box and attached to an ethylene Schlenk line. After pumping off the air and nitrogen and purging with ethylene, 4.649 mL (20 mmol) of PMAO was quickly added to the flask under about 35 kPa ethylene. After being stirred at RT overnight, the reaction mixture was quenched with 50 mL of a methanol solution of concentrated HCl (10% volume). The polymer was collected on a frit, washed with methanol and acetone thoroughly and then dried in vacuo overnight.

Method B: In the dry-box, 0.02 mmol of the bis (carboximidatonate) transition metal catalyst was placed in a Schlenk flask containing 35 mL of toluene and 4.649 mL (20 mol) of PMAO. The flask was sealed, removed from the dry-box and attached to an ethylene Schlenk line. After pumping off the air and nitrogen and purging with ethylene, the reaction mixture was stirred overnight at RT under about 35 kPa ethylene and then, quenched with 50 mL of a methanol solution of concentrated HCl (10% volume). The polymer was collected on a frit, washed with methanol and acetone thoroughly and then dried in vacuo overnight.

The polymers formed were linear high density PE, very high molecular weight and it was difficult get a GPC measurement. All the melt index tests showed no flow. The detailed data are listed in Table 1.

TABLE 1

Polymerization of Ethylene at 35 kPa

| Example | Method | Catalyst | PE (g) | Productivity (mol PE/mol complex) | $T_m$ (° C.) | $\Delta H_f$ (J/g) | Me/ 1000 CH$_2$ |
|---|---|---|---|---|---|---|---|
| 33 | A | 1 | 3.0086 | 4512 | 132.5 | 128.5 | 1.5 |
| 34 | A | 2 | 1.1464 | 1547 | 134.65 | 121.9 | 7.7 |
| 35 | A | 3 | 0.0664 | 103 | 135.09 | 196.8 | |
| 36 | A | 4 | 4.6791 | 7417 | 132.27 | 148.7 | |
| 37 | A | 5 | 1.0688 | 1797 | 134.45 | 151.8 | |
| 38 | A | 6 | 0.0575 | 101 | 133.51 | 181.7 | |
| 39 | B | 7 | 3.4416 | 6026 | 134.7 | 109.5 | |
| 40[a] | B | 10 | 1.6214 | 5594 | 134.97 | 169.4 | |

TABLE 1-continued

Polymerization of Ethylene at 35 kPa

| Example | Method | Catalyst | PE (g) | Productivity (mol PE/mol complex) | $T_m$ (° C.) | $\Delta H_f$ (J/g) | Me/ 1000 $CH_2$ |
|---|---|---|---|---|---|---|---|
| 41 | B | 11 | 1.5633 | 5975 | 134.78 | 174.8 | |
| 42 | B | 16 | 4.8137 | $5.42 \times 10^4$ | 134.63 | 175.7 | |
| 43[b] | B | 16 | 12.002 | $1.35 \times 10^5$ | 134.94 | 150.2 | |
| 44 | B | 19 | 0.3683 | 4458 | 134.49 | 173.4 | |
| 45 | B | 20 | 3.1324 | $2.41 \times 10^4$ | 134.81 | 165.7 | |

Note: [a]0.01 mmol catalyst and 1 hr. reaction; [b]0.003 mmol catalyst and 18 hr. reaction.

EXAMPLES 46–65
Polymerization of Ethylene at 6.9 MPa

In a dry-box, 0.002–0.01 mmol of the catalyst was placed glass vial and dissolved in 5 mL of 1,2,4-trichlorobenzene. The vial was cooled to −30° C. in the drybox freezer. PMAO was added to the vial on top of the frozen solution and the vial was then capped and sealed. Outside the drybox, the vials were placed into a shaker tube which was then shaken mechanically under high pressure ethylene for about 18 h. The white polymer was cut to pieces and added to a 100 mL of methanol solution of concentrated HCl (10% volume). The mixture was stirred overnight and filtered. The polymer was collected on a frit, washed with acetone and dried in vacuo.

The polymers formed were linear (for example: Me/1000$CH_2$ for example 47 is 3.5) high density PE, very high molecular weight and it was difficult to get GPC measurements. All the melt index tests showed no flow. The detailed data are listed in Table 2.

TABLE 2

Polymerization of Ethylene at High Pressure $C_2H_4$

| Example | Catalyst | PE (g) | Productivity (Mol PE /Mol complex.) | Pressure (MPa) | $T_m$ (° C.) | $\Delta H_f$ (J/g) |
|---|---|---|---|---|---|---|
| 46 | 1 | 9.3695 | $2.84 \times 10^4$ | 6.9 | 133.92 | 133.5 |
| 47 | 2 | 20.2679 | $6.35 \times 10^4$ | 6.9 | 137.01 | 164.5 |
| 48 | 3 | 2.1268 | 7293 | 3.5 | 137.48 | 160.8 |
| 49 | 5 | 5.46 | $1.74 \times 10^4$ | 3.5 | 136.04 | 146.2 |
| 50 | 6 | 3.6012 | $1.31 \times 10^4$ | 3.5 | 138.87 | 99.57 |
| 51 | 7 | 2.6388 | 9553 | 3.5 | 133.35 | 134.9 |
| 52 | 8 | 5.6004 | $2.02 \times 10^4$ | 3.5 | 135.86 | 204.5 |
| 53 | 9 | 10.3810 | $3.45 \times 10^4$ | 3.5 | 135.88 | 160.6 |
| 54 | 10 | 12.1552 | $3.71 \times 10^4$ | 3.5 | 131.69 | 147.6 |
| 55 | 11 | 8.9461 | $3.27 \times 10^4$ | 3.5 | 136.3 | 142.7 |
| 56 | 12 | 3.3109 | $1.13 \times 10^4$ | 3.5 | 137.25 | 124.5 |
| 57 | 14 | 0.0 | 0.0 | 3.5 | | |
| 58 | 15 | 10.0044 | $3.44 \times 10^4$ | 3.5 | 134.86 | 158.1 |
| 59 | 16 | 2.298 | $3.38 \times 10^4$ | 3.5 | 135.97 | 118.9 |
| 60 | 17 | 5.6168 | $2.36 \times 10^4$ | 3.5 | 134.5 | 160.4 |
| 61 | 18 | 0.9013 | 5502 | 3.5 | 135.69 | 147.7 |
| 62 | 21 | 13.2227 | $3.65 \times 10^4$ | 1.4 | 132.76 | 171.9 |
| 63 | 23 | 7.7944 | $2.23 \times 10^4$ | 1.4 | 131.82 | 190.3 |
| 64 | 4 | 1.1221 | 3795 | 1.4 | 131.22 | 79.62 |
| 65 | 5 | 1.6998 | 5486 | 1.4 | 135.45 | 146.2 |

The detailed data of polymerization with catalyst 10 under mixture of $H_2$ and $C_2H_4$ are listed in Table 3.

TABLE 3

Polymerization of Ethylene under $H_2/C_2H_4$

| Example | $H_2$ Pressure (kPa) | Total Pressure (MPa) | PE (g) | Productivity (mol PE/mol compound) | $T_m$ (° C.) | $\Delta H_f$ (J/g) | MI MI |
|---|---|---|---|---|---|---|---|
| 66 | 0 | 1.03 | 8.584 | $2.12 \times 10^5$ | 135.96 | 165.5 | no flow |
| 67 | 69 | 1.03 | 6.104 | $8.62 \times 10^4$ | 134.66 | 176.4 | no flow |
| 68 | 290 | 1.03 | 6.347 | $7.83 \times 10^4$ | 134.62 | 176.6 | no flow |
| 69[a] | 610 | 1.03 | 9.774 | $1.31 \times 10^5$ | 132.96 | 184.0 | no flow |
| 70[a] | 960 | 1.03 | 6.816 | $9.94 \times 10^4$ | 133.12 | 193.4 | no flow |

Note:
catalyst 10: 0.002 mmol, PMAO-IP: 2 mmol, toluene: 100 mL, 0.5–1 hr., R.T.
[a]60° C.

EXAMPLES 71–78
Copolymerization of 1-Hexene and Ethylene

In a dry-box, 0.02 mmol of the catalyst and 30 mL of 1,2,4-trichlorobezene or toluene were placed in a 100 mL Schlenk flask. The flask was cooled in a freezer in the dry-box and the 1,2,4-trichlorobenzene or toluene was frozen or cooled after 20 min. Then, 5 mL of 1-hexene and cocatalyst PMAO-IP were added to the flask. The flask was sealed, removed from the dry-box and attached to an ethylene Schlenk line. After pumping off the air and nitrogen and purging with ethylene, the reaction mixture was stirred 1 h or overnight depend on the rate of the polymer formation under 5 psi ethylene. The reaction was quenched with 50 mL of a methanol solution of concentrated HCl (10% volume). The polymer was collected on a frit, washed with methanol and acetone thoroughly, and then dried in vacuo overnight.

Most of the polymerizations produced high molecular weight rubbery polymer with high molecular weight and broad molecular weight distribution. The detailed data are listed in Table 4.

the flask. The flask was sealed, removed from the dry-box and attached to an ethylene Schlenk line. After pumping off the air and nitrogen and purging with ethylene, the reaction mixture was stirred 1 h or overnight depend on the rate of the polymer formation under 35 kPa ethylene. The reaction was quenched with 50 mL of a methanol solution of concentrated HCl (10% volume). The polymer was collected on a frit, washed with methanol and acetone thoroughly and then dried in vacuo overnight.

Most of the polymerizations produced high molecular weight rubbery polymer and wide molecular weight distribution (for Example 60, Mw=149517 and Mw/Mn=63). The detailed data are listed in Table 5.

TABLE 4

Copolymerization of Ethylene and 1-Hexene

| Example | Catalyst | PE (g) | $T_m$ (° C.) | $\Delta H_f$ (J/g) | Me/1000 $CH_2$ | Mw (Mw/Mn) | MI |
|---|---|---|---|---|---|---|---|
| 71[a] | 1 | 4.3914 | 123.29 | 51.73 | 32.8 | — | 0.03 |
| 72[a] | 2 | 1.0443 | 130.18 | 162.3 | 26.2 | — | no flow |
| 73[a] | 4 | 3.6378 | 122.99 | 34.9 | 71.3 | 240000 (17) | 0.6 |
| 74[a] | 5 | 0.893 | 128.33 | 135.3 | 10.2 | 195000 (multi modal) | — |
| 75[b] | 7 | 1.7465 | 119.85 | 46.19 | 52.9 | 557000 (6) | 0.075 |
| 76[b] | 11 | 0.4675 | 129.56 | 114.8 | 56.7 | — | — |
| 77[b] | 10 | 3.2786 | 124.15 | 4.436 | 62.5 | 69546 (17) | no flow |
| 78[c] | 20 | 3.7811 | 128.75 | 134.1 | 13.2 | — | no flow |

Note:
[a]1-hexene: 5 mL, 1,2,4-trichlorobenzene: 30 mL; [b]1-hexene: 10 mL, toluene: 20 mL; [c]1-hexene: 5 mL, toluene: 40 mL.

EXAMPLES 79–81

Copolymerization of 4-Methyl-1-Pentene and Ethylene

In a dry-box, 5 mL of 4-methyl-1-pentene, PMAO-IP, and 30 mL toluene were placed in a 100 mL Schlenk flask and stirred 5 min. Then, 0.02 mmol of the catalyst were added to

TABLE 5

Copolymerization of Ethylene and 4-Methyl-1-pentene

| Example | Catalyst | PE (g) | $T_m$ (° C.) | $\Delta H_f$ (J/g) | Me/1000 $CH_2$ | MI |
|---|---|---|---|---|---|---|
| 79 | 11 | 0.5236 | 127.09 | 152.6 | 62.9 | — |
| 80 | 16 | 4.8118 | 120.75 | 39.55 | 127 | 33 |
| 81 | 20 | 3.6868 | 128.67 | 138.8 | 22.2 | no flow |

EXAMPLES 82–90

Polymerization of Ethylene with Mixed Catalysts

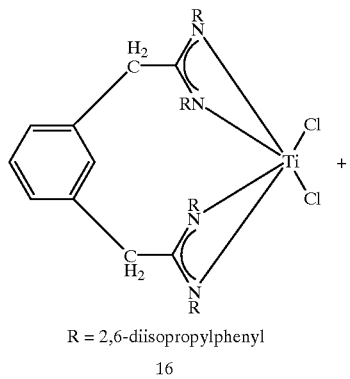

R = 2,6-diisopropylphenyl
16

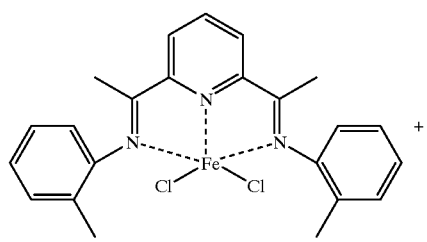

+

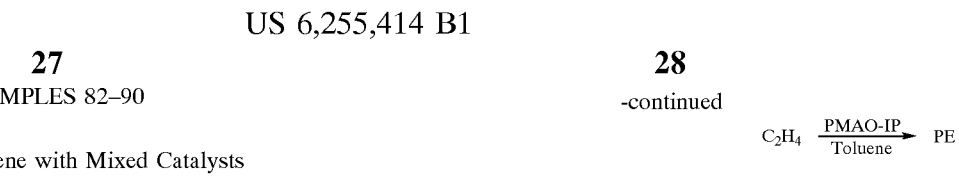

In a dry-box, 2 mmol PMAO—IP was added to 40 mL toluene and stirred 5 min. A toluene solution of 0.002–0.004 mmol of the amidinate catalyst 16 and tridentate Fe catalyst (in the above equation, which is believed to produce α-olefin in situ) were added to the flask. The flask was sealed, removed from the dry-box and attached to a Schlenk line which could be filled with ethylene. After pumping off the air and nitrogen and purging with ethylene, the reaction mixture was stirred ~3 h. under 35 kPa ethylene. The reaction was quenched with 50 mL of a methanol solution of concentrated HCl (10% volume). The polymer was collected on a frit, washed with methanol and acetone thoroughly and then dried in vacuo overnight.

The polyethylene formed was high in molecular weight, but Tm are decreased compare to the polymer produced from single amidinate catalysts. The detailed data are listed in Table 6.

TABLE 6

Polymerization of Ethylene by Mixed Catalysts

| Example | Catalyst ratio (Ti:Fe) | PE (g) | Productivity (mol PE/mol complex) | Tm (° C.) | $\Delta H_f$ (J/g) | Me/1000 $CH_2$ | MI |
|---|---|---|---|---|---|---|---|
| 82 | 1 | 11.7452 (4.6652) | $4.70 \times 10^4$ ($1.87 \times 10^4$) | 85.15 122.25 | 166.7 18.3 | 23.8 | 17 |
| 83[b] | 1 | 11.5747 (4.0383) | $5.37 \times 10^4$ ($1.87 \times 10^4$) | 87.44 119.03 | 199.8 15.9 | 26 | flow out |
| 84 | 30 | 3.555 | $1.06 \times 10^5$ | 126.47 | 147.1 | 10.37 | no flow |
| 85 | 15.2 | 3.1158 | $8.21 \times 10^4$ | 72.19 121.65 | 141.16 23.64 | 30 | 2.6 |
| 86 | 8 | 3.1737 | $8.38 \times 10^4$ | 124.12 | 170.2 | 12.2 | no flow |
| 87[c] | 9.8 | 0.3713 | 8825 | 78.45 114.28 125.82 | 22.84 117.14 30.52 | 17.9 | — |
| 88[c] | 3.65 | 1.9637 | $1.41 \times 10^4$ | 77.91 119.67 | 86.54 95.03 | 6.59 | 0.73 |
| 89[d] | 21 | 16.054 | $2.35 \times 10^5$ | 118.9 | 141.1 | 7.05 | no flow |
| 90[d] | 7.78 | 18.253 | $3.25 \times 10^5$ | 123.64 | 147.5 | 23.7 | no flow |

Note:
[a]mixture of α-olefin and polymer; [b]40° C.; [d]1.03 MPa, 80° C., catalyst 10 instead of 16.

EXAMPLES 91–94
Polymerization of 1-hexene

In a dry-box, 0.02 mmol of the catalyst and 7.66 mL of 1,2,4-trichlorobezene were placed in a 20 mL glass vial. Three mL of 1-hexene was added to the vial. Then, 2.34 mL (10 mmol) of PMAO was quickly added to the vial. After being stirred at RT 48 h, the reaction mixture was taken out from the dry-box and slowly poured to a beaker containing 50 mL of a methanol solution of concentrated HCl (10% volume). The colorless waxy polymer was separated from the methanol solution, washed with methanol and acetone thoroughly and then dried in vacuo overnight.

TABLE 7

Polymerization of 1-Hexene

| Example | Catalyst | Polymer (g) | Productivity (mol PH/mol complex) | $M_w$ ($M_w/M_n$) |
|---|---|---|---|---|
| 91 | 1 | 0.2001 | 118 | |
| 92 | 2 | 0.2803 | 165 | 50900 (47) |
| 93 | 4 | 0.3356 | 305 | 2130 (15) |
| 94 | 5 | 0.0838 | 57 | |

EXAMPLES 95–97
Polymerization of Propylene

In a dry-box, 0.01 mmol of the catalyst was placed in a 50 mL Schlenk flask with threaded joints and 20 mL of toluene was added to dissolve or partially dissolve the catalyst. The flask was sealed, removed from the dry-box and attached to an propylene line. After purging with nitrogen and propylene, 2.33 mL (10 mmol) of PMAO was quickly added to the flask under about 35 kPa propylene. After being stirred at RT 48 h, the reaction mixture was quenched with 50 mL of a methanol solution of concentrated HCl (10% volume). The polymer was collected on a frit, washed with methanol and acetone thoroughly and then dried in vacuo overnight.

TABLE 8

Polymerization of propylene

| Example | Catalyst | Polymer (g) | Productivity (mol PP/mol complex) | $M_w$ ($M_w/M_n$) |
|---|---|---|---|---|
| 95 | 1 | 0.2184 | 503 | 180000 (multi modal) |
| 96 | 2 | 0.2344 | 366 | 260000 (multi modal) |
| 97 | 5 | 0.0931 | 188 | 188000 (multi modal) |

EXAMPLES 98–99
Polymerization of Norbornene

In a dry-box, to a 20 mL glass vial containing 2.26 g (0.04 mol) of norbornene and 3 mL of toluene, was added 2.34 mL (10 mmol) PMAO. The mixture was stirred 5 min and then 4.66 mL of a toluene suspension of the catalyst (0.02 mmol) was added. After being stirred at RT 24 h, the reaction mixture was taken out from the dry-box and slowly poured to a beaker containing 50 mL of a methanol solution of concentrated HCl (10% volume). The polymer was collected on a frit, washed with methanol and acetone thoroughly and then dried in vacuo overnight.

TABLE 9

Polymerization of norbornene

| Example | Catalyst | Polymer (g) (Conversion %) | Productivity (mol PN/mol complex) | $M_w$ ($M_w/M_n$) |
|---|---|---|---|---|
| 98 | 1 | 0.4325 (19.1) | 333 | 96500 (multi modal) |
| 99 | 2 | 0.5072 (22.4) | 227 | 133000 (multi modal) |

EXAMPLE 100
Preparation of Azobenzene-Bridged Bis-guanidinate Ligand and Zirconium Complex Azobenzene (2.73 g, 15 mmol) was dissolved in THF (30 mL) under nitrogen in a drybox. Lithium metal (0.36 g, 50 mmol) was added to the solution. The orange changed to green before turning to orange-brown. After three h stirring, the solution was added slowly to a solution of bis (trimethylsilyl)carbodiimide (5.59 g, 30 mmol) causing a slight lightening of the solution color. Stirring was continued for 30 min.

The resulting solution was added slowly to a THF (30 mL) solution of $ZrCl_4$ (3.5 g, 15 mmol). There was a slight darkening to dark beige. The THF was removed under vacuum and the solid was extracted with methylene chloride. Filtration through filter aid gave a yellow-gray solution which was taken to dryness. The solid was then suspended in ether, filtered and dried under vacuum. Yield: 1.7g The ether solution was stripped to dryness yielding a very small quantity of a white solid which crystallized like an organic. The $^1$H NMR indicated the presence of phenyl and trimethylsilyl resonances in a 1:1 ratio with no other signals. The solid was taken up in ether and placed in the drybox freezer where it crystallized. X-ray analysis demonstrated that it was 1,2-diphenyl-1,2-bis(trimethylsilyl)hydrazine.

EXAMPLE 101
Polymerization With an Azobenzene-Bridged Bis-guanidinate Zirconium Complex In toluene (35 mL), catalyst (0.0122 g, 0.02 mmol) with 2.22 mL of MMAO (10 mmol) at RT and 1 atm ethylene overnight yielded 1.51 g of HDPE polyethylene.

EXAMPLE 102

Preparation of Azobenzene-Bridged Bis-guanidinate Ligand and Titanium Complex Azobenzene (2.73 g, 15 mmol) was dissolved in THF (30 mL) under nitrogen in a drybox. Lithium metal (0.36 g, 50 mmol) was added to the solution. The orange changed to green before turning to orange-brown. After three h stirring, the solution was added slowly to a solution of bis(trimethylsilyl)carbodiimide (5.59 g, 30 mmol) causing a slight lightening of the solution color. Stirring was continued for 30 min.

The resulting solution was reacted with a THF (30 mL) solution of $TiCl_4$ 2THF (3.5 g, 15 mmol). There was a rapid darkening to red-brown. The THF was removed under vacuum and the solid was extracted repeatedly with methylene chloride. Filtration through filter aid gave a deep red-brown solution which was taken to dryness. Yield: 1.23 g. Washing with ether yielded a trace material having the same NMR as observed for diphenyl-bis-trimethylsilylhydrazine as noticed in the zirconium reaction.

EXAMPLE 103

Polymerization With an Azobenzene-Bridged Bis-guanidinate Titanium Complex

In toluene (35 mL), 0.02 mmol of catalyst with 2.22 mL of MMAO (10 mmol) at RT and 1 atm ethylene overnight yielded 0.38 g of polyethylene. In trichlorobenzene, 0.0050 g of catalyst with 3 mL of MMAO at 50° C. and 1.38 MPa ethylene yielded 4.112 g of polyethylene, which was "No flow" MI and had 10.8 Me/1000CH$_2$.

EXAMPLE 104

Preparation of Butadiene-bridged Bis-amidinate Ligand and Titanium Complex

Magnesium butadiene (15 mmol) is prepared according to the method of Yasuda (J. Organomet. Chem., 113, 201 (1976). The resulting solution is added slowly to a solution of bis(trimethylsilyl)carbodiimide (5.59 g, 30 mmol). Stirring is continued for 30 min.

The resulting solution is reacted with a THF (30 mL) solution of $TiCl_4$ 2THF (3.5 g, 15 mmol). The THF is removed under vacuum and the solid is extracted repeatedly with methylene chloride. Filtration through filter aid gives a deep red-brown solution which is taken to dryness yielding a powder.

EXAMPLE 105

Polymerization With a Butadiene-Bridged Bis-amidinate Titanium Complex

In toluene (35 mL), 0.02 mmol of catalyst is reacted with 2.22 mL of MMAO (10 mmol) at RT and pressurized with 1 atm ethylene. The resulting polymerization yields high density polyethylene.

What is claimed is:

1. A process for the polymerization of olefins, comprising the step of contacting, at a temperature of about −50° C. to about +250° C.:

(a) an olefin selected from the group consisting of ethylene, an α-olefin, a styrene, a cyclopentene, and a norbornene; and (b) an active polymerization catalyst comprising a transition metal complex of a ligand of the formula (XI)

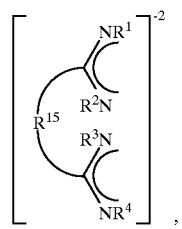

(XI)

wherein:

said transition metal is Ti, Zr, Hf V, Cr, Sc, Y or a rare earth metal;

$R^1$, $R^2$, $R^3$ and $R^4$ are each independently hydrocarbyl, substituted hydrocarbyl or silyl;

$R^{15}$ is o-phenylene, 1,2-naphthylene, 2,3-naphthylene, 1,8-naphthylene, 1,2-cyclohexylene,

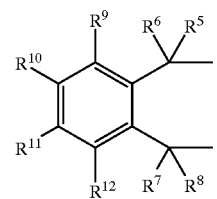

(XII)

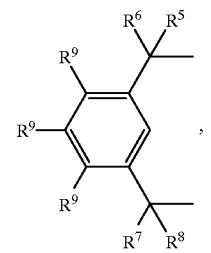

(XXIII)

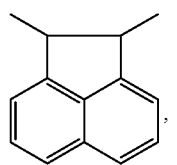

(XIII)

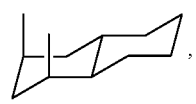

(XVI)

(XVII)

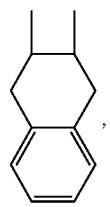

(XVIII)

 (IX)

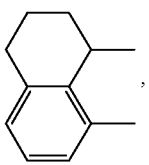 (XX)

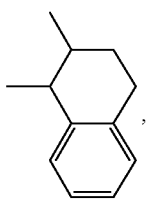 (XXI)

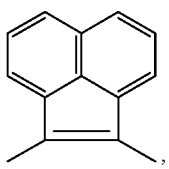 (XXII)

—CR$^{16}_2$(CR$^{16}_2$)$_q$CR$^{16}_2$—(XV), or a divalent organic moiety containing one or more nitrogen atoms;

R$^1$, R$^6$, R$^7$ and R$^8$ are each independently hydrogen, hydrocarbyl or substituted hydrocarbyl, provided that either or both of the pairs R$^5$ and R$^6$, and R$^7$ and R$^8$ taken together may form a ring;

R$^9$, R$^{10}$, R$^{11}$ and R$^{12}$ are each independently hydrogen, hydrocarbyl, substituted hydrocarbyl, or a functional group, provided that any two of R$^9$, R$^{10}$, R$^{11}$ and R$^{12}$ vicinal to one another may form a ring;

R$^{16}$ is hydrogen and q is 4.

2. The process as recited in claim 1, wherein the transition metal complex is a compound of the formula (X)

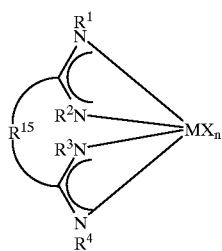 (X)

wherein:

each X is independently an anion;

M is Ti, Zr, Hf, V, Cr, Sc, Y or a rare earth metal; and n is an integer equal to the valence of M minus 2.

3. The process as recited in claim 2, wherein the olefin, compound of the formula (X) and a compound W are contacted, wherein W is a neutral Lewis acid capable of abstracting an X$^-$ from the compound of the formula (X) to form WX$^-$, provided that the anion formed is a weakly coordinating anion, or a cationic Lewis or Bronsted acid whose counterion is a weakly coordinating anion; and provided that when none of X is alkyl, acyl or hydride, said compound W is capable of transferring hydride or alkyl to M.

4. The process as recited in claim 1, wherein R$^{15}$ is (XII) or (XXIII).

5. The process as recited in claim 2, wherein R$^{15}$ is (XII) or (XXIII).

6. The process as recited in claim 3, wherein R$^{15}$ is (XII) or (XXIII).

7. The process as recited in claim 1, wherein R$^1$ R$^2$, R$^3$ and R$^4$ are each independently alkyl or silyl.

8. The process as recited in claim 2, wherein R$^1$, R$^2$, R$^3$ and R$^4$ are each independently alkyl or silyl.

9. The process as recited in claim 3, wherein R$^1$, R$^2$, R$^3$ and R$^4$ are each independently alkyl or silyl.

10. The process as recited in claim 1, wherein R$^5$, R$^6$, R$^7$ and R$^8$ are each independently alkyl or hydrogen; and R$^9$, R$^{10}$, R$^{11}$ and R$^{12}$ are all hydrogen.

11. The process as recited in claim 2, wherein R$^5$, R$^6$, R$^7$ and R$^8$ are each independently alkyl or hydrogen; and R$^9$, R$^{10}$, R$^{11}$ and R$^{12}$ are all hydrogen.

12. The process as recited in claim 3, wherein R$^5$, R$^6$, R$^7$ and R$^8$ are each independently alkyl or hydrogen; and R$^9$, R$^{10}$, R$^{11}$ and R$^{12}$ are all hydrogen.

13. The process as recited in claim 1, wherein said olefin comprises ethylene.

14. The process as recited in claim 4, wherein said olefin comprises ethylene.

15. The process as recited in claim 13, wherein said olefin consists essentially of ethylene.

16. The process as recited in claim 13, wherein a catalyst which oligomerizes ethylene to an α-olefin is also present.

17. The process as recited in claim 2, wherein said olefin comprises ethylene.

18. The process as recited in claim 5, wherein said olefin comprises ethylene.

19. The process as recited in claim 17, wherein said olefin consists essentially of ethylene.

20. The process as recited in claim 17, wherein a catalyst which oligomerizes ethylene to an α-olefin is also present.

21. The process as recited in claim 3, wherein said olefin comprises ethylene.

22. The process as recited in claim 6, wherein said olefin comprises ethylene.

23. The process as recited in claim 21, wherein said olefin consists essentially of ethylene.

24. The process as recited in claim 21, wherein a catalyst which oligomerizes ethylene to an α-olefin is also present.

25. The process as recited in claim 1, wherein the transition metal is Zr or Ti.

26. The process as recited in claim 2, wherein the transition metal is Zr or Ti.

27. The process as recited in claim 3, wherein the transition metal is Zr or Ti.

28. The process as recited in claim 4, wherein the transition metal is Zr or Ti.

29. The process as recited in claim 5, wherein the transition metal is Zr or Ti.

30. The process as recited in claim 6, wherein the transition metal is Zr or Ti.

31. The process as recited in claim 1, wherein another active olefin polymerization catalyst is present.

32. The process as recited in claim 4, wherein another active olefin polymerization catalyst is present.

33. The process as recited in claim 31, wherein the another active olefin polymerization catalyst comprises a late transition metal catalyst, a Ziegler-Natta catalyst and/or a metallocene catalyst.

34. The process as recited in claim 32, wherein the another active olefin polymerization catalyst comprises a late transition metal catalyst, a Ziegler-Natta catalyst and/or a metallocene catalyst.

35. The process as recited in claim 2, wherein another active olefin polymerization catalyst is present.

36. The process as recited in claim 5, wherein another active olefin polymerization catalyst is present.

37. The process as recited in claim 35, wherein the another active olefin polymerization catalyst comprises a late transition metal catalyst, a Ziegler-Natta catalyst and/or a metallocene catalyst.

38. The process as recited in claim 36, wherein the another active olefin polymerization catalyst comprises a late transition metal catalyst, a Ziegler-Natta catalyst and/or a metallocene catalyst.

39. The process as recited in claim 3, wherein another active olefin polymerization catalyst is present.

40. The process as recited in claim 6, wherein another active olefin polymerization catalyst is present.

41. The process as recited in claim 39, wherein the another active olefin polymerization catalyst comprises a late transition metal catalyst, a Ziegler-Natta catalyst and/or a metallocene catalyst.

42. The process as recited in claim 40, wherein the another active olefin polymerization catalyst comprises a late transition metal catalyst, a Ziegler-Natta catalyst and/or a metallocene catalyst.

* * * * *